(12) United States Patent
Matsuzaki et al.

(10) Patent No.: US 6,335,472 B1
(45) Date of Patent: *Jan. 1, 2002

(54) METHOD OF HYDROGENATING EPOXIDIZED $C_6$—$C_{12}$ CYCLOHYDROCARBON COMPOUNDS

(75) Inventors: Tokuo Matsuzaki; Yasuo Nakamura; Takumi Manabe; Takato Nakamura; Nobuyuki Kuroda; Hiroshi Shiraishi, all of Ube (JP)

(73) Assignee: UBE Industries, Ltd., Ube (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/469,376

(22) Filed: Dec. 22, 1999

(30) Foreign Application Priority Data

Dec. 28, 1998 (JP) ............................. 10-372794
Jun. 9, 1999 (JP) ............................. 11-162349
Sep. 27, 1999 (JP) ............................. 11-271583

(51) Int. Cl.[7] ............................. C07C 49/23
(52) U.S. Cl. ................. 568/338; 568/361; 568/821; 568/822
(58) Field of Search ................. 568/338, 361, 568/322, 329, 822, 835, 823, 821

(56) References Cited

FOREIGN PATENT DOCUMENTS

EP      0 192 298      8/1986
GB      1 273 689      6/1970

OTHER PUBLICATIONS

J. Mol. Catal. vol. 69, P95–103 (1991).

Synthetic Communications, 25 (15), P2267–2273 (1995).

CA:123:339560 abs of Tetrahedron Lett by Cho 36(34), pp 6009–12, 1995.*

CA:123:116175 abs of Neftehimiya by Antonova 35(1) pp 49–55, 1995.*

Balbolov, E. KH. et al.: New Routes to Cyclododecanone; Russ J. Gen. Chem. (1997), 67(6), 921–926.

Accrombessi, Georges C. et al., "Mechanism 1–6 of the Liquid–Phase Catalytic Hydrogenolysis...Epoxides"J. Org. Chem (1980), 45(21), 4139–43, XP00217472.

Chemical Abstracts, vol. 85, No. 7 Aug. 16, 1976 XP–00215473.

* cited by examiner

Primary Examiner—Jean F. Vollano
(74) Attorney, Agent, or Firm—Morgan, Lewis & Bockius LLP

(57) ABSTRACT

Epoxidized $C_6$–$C_{12}$ cyclohydrocarbon compounds, for example, epoxidized $C_6$–$C_{12}$ cycloalkanes, cycloalkenes and/or cycloalkadienes are converted to cycloalkanols, cycloalkanones and cycloalkanes by hydrogenating the epoxidized $C_6$–$C_{12}$ cyclohydrocarbon compounds with hydrogen under a pressure of 0.1 to 5.4 MPa at a temperature of 100 to 280° C. in the presence of a catalyst containing at least one platinum group metal, for example, Pd or Ru.

9 Claims, No Drawings

METHOD OF HYDROGENATING EPOXIDIZED $C_6$–$C_{12}$ CYCLOHYDROCARBON COMPOUNDS

BACKGROUND OF THE INVENTION

1. Field of the Invention

The present invention relates to a method of hydrogenating epoxidized $C_6$–$C_{12}$ cyclohydrocarbon compounds. More particularly, the present invention relates to a method of hydrogenating epoxidized $C_6$–$C_{12}$ cyclohydrocarbon compounds, to produce, for example, $C_6$–$C_{12}$ cycloalkanols and/or $C_6$–$C_{12}$ cycloalkanones. The $C_6$–$C_{12}$ cycloalkanols, for example, cyclododecanol and the $C_6$–$C_{12}$ cycloalkanones, for example, cyclododecanone, are useful as intermediate compounds for producing lactams, lactones and polycarboxylic acids, which are useful for polyamides and polyesters for synthetic resins and synthetic fibers.

2. Description of the Related Art

It is known that a mixture of a cycloalkanone with a cycloalkanol can be produced by oxidizing a cycloalkane with air in the presence of a catalyst comprising boric acid. In this method, the air oxidation is effected in successive reactions and thus a plurality of by-products are produced during the reactions. Thus, the conversion of the cycloalkane must be low and the yield of the target mixture of cycloalkanol with cycloalkanone is usually low. For example, in the air oxidation of cyclododecane in the presence of a boric acid catalyst, it is known that the mixture of cyclododecanone with cyclododecanol is obtained in a yield of 20 to 25%. Also, it is known that when cyclohexane is oxidized with air, the yield of the mixture of cyclohexanone with cyclohexanol is several %.

Also, it is known that epoxidized cycloalkanes and/or epoxidized cycloalkenes can be produced by epoxidizing corresponding cycloalkenes with a high yield. If the epoxidized compounds can be converted to corresponding cycloalkanones and cycloalkanols with a high efficiency, the cycloalkanones and the cycloalkanols can be expected to be obtained at a high yield. However, only a small number of reports can be found on methods of converting an epoxidized cycloalkane and/or an epoxidized cycloalkene to a mixture of cycloalkanone with cycloalkanol. For example, J. Mol. Catal., Vol. 69, pages 69 to 103 (1991) discloses a method of hydrogenating a monoepoxycyclododecadiene with hydrogen in the presence of a catalyst comprising palladium carried on a carrier consisting of γ-alumina, under a hydrogen gas pressure of 1.3 MPa at a temperature of 90° C. In this method, cyclododecanol was produced with a yield of 20% or less and no cyclododecanone was produced. When a catalyst comprising palladium carried on a carrier consisting of titania or silica was used in place of the above-mentioned palladium catalyst carried on γ-alumina, the yield of cyclododecanol was low and unsatisfactory.

Also, the Drafted Report of 24th Symposium of Development in Reaction and Synthesis, Nov. 5 to 6, 1998, page 68, discloses a method of hydrogenating 1,2-epoxy-5,9-cyclododecadiene with hydrogen at ambient atmospheric pressure and room temperature in the presence of a catalyst comprising palladium carried on a carrier consisting of a carbon material. In this method, cyclododecanol was produced with a yield of 5% and no cyclododecanone was obtained.

Further, Neftekhimiya, 16(1), 119—119, (1976) discloses a method in which 1,2-epoxy-5,9-cyclododecadiene is brought into contact with hydrogen in the presence of a palladium-carrying catalyst under a hydrogen pressure of 9.06 MPa (80 atmospheres) at a temperature of 140° C. By this method, 49.5% of epoxycyclododecane, 33.3% of cyclododecanol and 3.4% of cyclododecanone were obtained. In this method, the yields of cyclododecanol and cyclododecanone were unsatisfactory.

As mentioned above, when the 1,2-epoxy-5,9-cyclododecadiene is hydrogenated with a hydrogen gas by the known methods, the yields of cyclododecanol and cyclododecanone are very low and unsatisfactory.

As an analogous method, Synthetic Communication, 25(15), pages 2267 to 2273 (1995) discloses a method of synthesizing cyclohexanol by hydrogenating 1,2-epoxy-5,9-cyclohexane. In this method, 1,2-epoxy-5,9-cyclohexane was reduced with ammonium formate ($HCOONH_4$) in the presence of a catalyst comprising palladium carried on a carrier consisting of activated carbon, and as a result, cyclohexanol was produced with a yield of 50% and no cyclohexanone was obtained. This method is, however, disadvantageous in that the ammonium formate ($HCOONH_4$) which is used as a hydrogen-supply source, is expensive, and the yields of cyclohexanol and cyclohexanone are low although the expensive hydrogen-supply source is employed. Therefore, this method is practically unusable as a production method of cycloalkanone and cycloalkanol which are useful for producing lactam materials.

Accordingly, no method of producing $C_6$–$C_{12}$ cycloalkanols and $C_4$–$C_{12}$ cycloalkanones with a satisfactory yield, from epoxidized $C_6$–$C_{12}$ cyclohydrocarbon compounds, for example, $C_6$–$C_{12}$ cycloalkanes cycloalkadienes and/or cycloalkenes, has been known.

SUMMARY OF THE INVENTION

An object of the present invention is to provide a method of hydrogenating epoxidized $C_6$–$C_{12}$ cyclohydrocarbon compounds in the presence of a platinum group metal-containing catalyst with a high efficiency.

Another object of the present invention is to provide a method of hydrogenating epoxidized $C_6$–$C_{12}$ cyclohydrocarbon compounds in the presence of a platinum group metal-containing catalyst in one single-step reaction with a high yield of hydrogenated cyclohydrocarbon compounds.

The above-mentioned objects can be attained by the method of the present invention.

The method of the present invention for hydrogenating epoxidized $C_6$–$C_{12}$ cyclohydrocarbon compounds, comprising bringing a starting material comprising at least one epoxidized cyclohydrocarbon compound having 6 to 12 carbon atoms into contact with hydrogen under a hydrogen pressure of 0.1 to 5.4 MPa on gauge at a temperature of 100 to 280° C. in the presence of a catalyst comprising a catalytic metal component comprising at least one platinum group metal.

In the hydrogenating method of the present invention, the starting material may comprise at least one member selected from the group consisting of monoepoxy $C_6$–$C_{12}$ cycloalkenes, monoepoxy $C_6$–$C_{12}$ cycloalkanes and monoepoxy $C_6$–$C_{12}$ cycloalkadiens and the resultant hydrogenation reaction product may comprise at least one member of $C_6$–$C_{12}$ cycloalkanones and $C_6$–$C_{12}$ cycloalkanols.

In the hydrogenating method of the present invention, the catalytic metal component of the catalyst is optionally carried on an inert carrier comprising at least one member selected from the group consisting of activated carbon, alumina, silica, silica-alumina, titania, zeolites and spinel, especially α-alumina.

In an embodiment of the hydrogenating method of the present invention, the starting material comprises at least one member selected from the group consisting of monoepoxy cyclododecanes, monoepoxy cyclododecenes and monoepoxy cyclododecadienes, and is brought into contact with hydrogen under a hydrogen pressure of 0.1 to 5.4 MPa on gauge at a temperature of 100 to 280° C., in the presence of a catalyst comprising, as a catalytic metal component, at least one metal selected from the group consisting of palladium and ruthenim, to produce cyclododecanol and cyclododecanone.

In another embodiment of the hydrogenating method of the present invention, the starting material comprises 1,2-epoxy-5,9-cyclododecadiene and is brought into contact with hydrogen under a hydrogen pressure of 0.1 to 3.9 MPa on gauge at a temperature of 100 to 280° C., in the presence of a catalyst comprising, as a catalytic metal component, at least one platinum group metal, to produce cyclododecanone.

In still another embodiment of the hydrogenating method of the present invention, the catalytic metal component of the catalyst is carried on an inert carrier comprising a-alumina, and the starting material is hydrogenated into a mixture of $C_6$–$C_{12}$ cycloalkanone with $C_6$–$C_{12}$ cycloalkanol.

DESCRIPTION OF THE PREFERRED EMBODIMENTS

In the method of the present invention, hydrogenating epoxidized $C_6$–$C_{12}$ cyclohydrocarbon compounds are hydrogenated by bringing a starting material comprising at least one epoxidized cyclohydrocarbon compound having 6 to 12 carbon atoms into contact with hydrogen under a hydrogen pressure of 0.1 to 5.4 MPa on gauge at a temperature of 100 to 280° C. in the presence of platinum group metal-containing catalyst.

The starting material for the method of the present invention comprises at least one member selected from epoxidized cyclohydrocarbon compounds having 6 to 12 carbon atoms, which compounds may be saturated or unsaturated.

The epoxidized $C_6$–$C_{12}$ cyclohydrocarbon compounds are preferably selected from monoepoxy $C_6$–$C_{12}$ cycloalkanes, monoepoxy $C_6$–$C_{12}$ cycloalkenes and monoepoxy $C_6$–$C_{12}$ cycloalkadienes. The epoxidized $C_6$–$C_{12}$ cyclohydrocarbon compounds may have two or more epoxy groups.

In the method of the present invention, the hydrogenation reaction product comprises at least one member selected from the group consisting of $C_6$–$C_{12}$ cycloalkanols and $C_6$–$C_{12}$ cycloalkanones, corresponding to the starting epoxidized $C_6$–$C_{12}$ cyclohydrocarbon compound.

The epoxidized $C_6$–$C_{12}$ cycloalkanes include epoxidized cyclohexanes, epoxidized cycloheptanes, epoxidized cyclooctanes, epoxidized cyclononanes, epoxidized cyclodecanes, epoxidized cycloundecanes and epoxidized cyclododecanes.

The epoxidized $C_6$–$C_{12}$ cycloalkenes include epoxidized cyclohexenes, epoxidized cycloheptenes, epoxidized cyclooctenes, epoxidized cyclononenes, epoxidized cyclodecenes, epoxidized cycloundecenes and epoxidized cyclododecenes.

The epoxidized $C_6$-$C_{12}$ cycloalkadienes include epoxidized cyclohexadienes, epoxidized cycloheptadienes, epoxidized cyclooctadienes, epoxidized cyclononadienes, epoxidized cyclodecadienes, epoxidized cycloundecadienes, and epoxidized cyclododecadienes, which may be in cis-, trans- and other structures.

In the method of the present invention, the resultant $C_6$–$C_{12}$ cycloalkanols include cyclohexanol, cycloheptanol, cyclooctanol, cyclononanol, cyclodecanol, cycloundecanol and cyclododecanol. Also, the cycloalkanones include cyclohexanone, cycloheptanone, cyclooctanone, cyclononanone, cyclodecanone, cycloundecanone and cyclododecanone.

In the method of the present invention, the starting material may contain impurities, for example, non-epoxidized cyclohydrocarbon compounds, for example, cycloalkanes, cycloalkanols and cyclalkanones. In the method of the present invention, the platinum group metal-containing catalyst is in the state of a solid and comprises, as a catalytic metal component, at least one member selected from ruthenium, rhodium, palladium, osmium, iridium and platinum, preferably ruthenium and palladium, more preferably palladium.

The platinum group metal-containing catalyst optionally contains an inert carrier on which the catalytic metal component is carried. The inert carrier preferably comprises at least one member selected from the group consisting of activated carbon, alumina, silica, silica-alumina, zeolite and spinel.

The solid platinum group metal-containing catalyst is preferably in the form of fine particles, having an average particle size of 1 to 1000 μm, more preferably 10 to 100 μm, or in the form of pellets having an average length of 1 to 10 mm and an average diameter of 2 to 6 mm. In the catalyst having the inert carrier, the catalytic metal component is preferably in an amount of 0.1 to 20% by weight, more preferably 0.5 to 10% by weight, based on the weight of the inert carrier.

In the catalyst for the hydrogenating method of the present invention, the catalytic metal component may be located on the surface or in the inside or both on the surface and in the inside, of the inert carrier.

In the hydrogenating method of the present invention, the catalyst is preferably employed in an amount of 0.00001 to 0.1 mole, more preferably 0.00005 to 0.01 mole, in terms of the total platinum group metal atoms, per mole of the starting material.

In the hydrogenating method of the present invention, the catalytic reaction of the starting material with hydrogen may be effected in an organic liquid reaction medium which is non-reactive with hydrogen and the starting material under the reaction conditions. The liquid medium preferably comprises at least one member selected from, liquid hydrocarbons, for example, n-hexane, n-heptane, n-tetradecane and cyclohexane; liquid ethers, for example, tetrahydrofuran and dioxane; liquid alkanols, for example, methyl alcohol, ethyl alcohol and t-butyl alcohol and t-aryl alcohol; liquid esters, for example, ethyl acetate and butyl acetate. These liquid compounds may be employed alone or in a mixture of two or more thereof. The liquid medium is preferably used in an amount of 20 times or less, more preferably 10 times or less, the weight of the starting material.

The liquid medium may make control of the reaction easy.

In the hydrogenating method of the present invention, the starting material is introduced into a reactor and is brought into contact with a hydrogen gas introduced into the reactor under a hydrogen pressure of 0.1 to 5.4 MPa on gauge, preferably 0.2 to 5.4 MPa on gauge, more preferably 0.2 to 3.9 MPa on gauge, at a temperature of 100 to 280° C., preferably 100 to 230° C., more preferably 120 to 200° C., in the presence of the platinum group metal-containing catalyst.

When the hydrogen pressure is less than 0.1 MPa on gauge, the reaction time necessary to complete the hydrogenating reaction becomes too long and thus is practically disadvantageous. When the hydrogen pressure is more than 5.4 MPa on gauge, the target product is obtained with too low a yield.

When the reaction temperature is less than 100° C., the yield of the target product is unsatisfactory, and when the reaction temperature is more than 280° C., undesired side reactions occur to cause undesired by-products to be produced.

There is no limitation to the type of reactor for the hydrogenating reaction. The reaction can be carried out in a liquid phase, catalyst-suspension bed type reactor or a catalyst-fixed bed type reactor. In the catalyst suspension bed type reactor, the catalyst in the form of fine particles is used. Also, in the catalyst-fixed bed type reactor, the catalyst in the form of pellets in employed. In the catalyst-fixed bed type reactor, the hydrogenation of the starting material may be effected by a trickle reaction, a liquid phase reaction or a gas phase reaction.

After the hydrogenation reaction is completed, the reaction product-containing mixture is subjected to a procedure for collecting and refining the target product by, for example, distillation and crystallization.

In an embodiment (1) of the method of the present invention, a starting material comprising at least one monoepoxy $C_{12}$ cyclohydrocarbon compound selected from monoepoxy saturated and unsaturated $C_{12}$ cyclohydrocarbon compounds, for example, monoepoxy cyclododecane, monoepoxy cyclododecene and monoepoxy cyclododecadiene, is brought into contact with hydrogen in the presence of a catalyst comprising, as a catalytic metal component, at least one member selected from platinum group metals, preferably palladium and ruthenium, under a hydrogen pressure of 0.1 to 5.4 MPa on gauge, preferably 0.5 to 5.4 MPa on gauge and more preferably 1.0 to 5.4 MPa on gauge at a temperature of 100 to 280° C., preferably 120 to 230° C., more preferably 120 to 200° C. to produce cyclododecanol and cyclododecanone. In this embodiment (1), the catalyst preferably has an inert carrier on which the catalytic metal component is carried. The carrier preferably comprises at least one member selected from activated carbon, aluminum, silica, zeolite and spinel, and the catalytic metal component (palladium or ruthenium) are carried, in an amount of 1 to 20% by weight, on the surface and/or in the inside of the carrier.

The hydrogenation reaction may be carried out in the liquid reaction medium as mentioned above.

In another embodiment (2) of the method of the present invention, 1,2-epoxy-5,9-cyclododecadiene, which may be in cis- or trans type, is brought into contact with hydrogen in the presence of a catalyst comprising, as a catalytic metal component, at least one platinum group metal under a hydrogen pressure of 0.1 to 3.9 MPa on gauge preferably 0.2 to 3.9 MPa on gauge, more preferably 0.2 to 2.9 MPa on gauge at a temperature of 100 to 280° C., preferably 100 to 230° C., more preferably 120 to 200° C., to produce cyclododecanone. In this embodiment, the catalytic metal component of the catalyst comprises palladium and/or ruthenium. The catalytic metal component may be carried on the surface and/or in the mind of the carrier as mentioned above.

In this embodiment (2), the catalyst is preferably used in an amount, in terms of platinum group metal atoms, of 0.00001 to 0.1 mole, more preferably 0.00005 to 0.01 mole, per mole of 1,2-epoxy-5,9-cyclododecadiene.

The hydrogenation reaction of the embodiment may be carried out in the liquid reaction medium as mentioned above.

In still another embodiment (3) of the present invention, a starting material comprising at least one epoxidized $C_6$–$C_{12}$ cyclohydrocarbon compound, for example, an epoxy cycloalkane and/or an epoxy cycloalkene, is brought into contact with hydrogen in the presence of a catalyst comprising a catalytic platinum group metal component and a carrier comprising α-alumina, under a hydrogen pressure of 0.1 to 5.4 MPa on gauge at a temperature of 100 to 280° C., to produce cycloalkanone and a cycloalkanol.

In this embodiment (3), preferably the starting material comprises epoxycyclododecane, epoxycyclododecadiene and/or epoxycyclododecene, and the resultant product comprises cycododecanone and cyclododecanol.

In this embodiment (3), the catalytic metal component is carried on the surface and/or in the inside of the α-alumina carrier. The catalytic metal component is preferably in the form of fine particles having an average particle size of 0.1 nm to 1000 nm.

The carrier of the catalyst for this embodiment comprises α-alumina which has an α-alumina crystalline structure confirmed by the X-ray diffraction pattern. The α-alumina may contain several % by weight or less of impurities, for example, Na, Mg, Fe, $SiO_2$ which may not affect the catalytic activity of the α-alumina. Sometimes, an alkaline metal and/or an alkaline earth metal enhance the catalytic activity of the α-alumina.

There is no limitation to the surface properties and fine pore properties of the α-alumina carrier. Usually, the α-alumina carrier preferably has a specific surface area of 20 $m^2$/g or less, more preferably 1 to 20 to $m^2$/g, and an average pore size of 50 to 500 μm.

In the catalyst, the catalytic metal component is preferably in an amount of 0.1 to 20%, more preferably 0.5 to 10% by weight, based on the weight of the α-alumina carrier. When the amount of the catalytic metal component is less than 0.1% by weight based on the α-alumina carrier, the resultant catalyst may exhibit an insufficient catalytic activity. If the amount of the catalytic metal component is more than 20% by weight, the expensive platinum metal is employed with low efficiency.

The catalyst for the embodiment (3) may be in the form of fine particles or in the form of pellets. The fine particles preferably have an average particle size of 1 μm to several hundreds μm and are useful for liquid phase, catalyst-suspension bed type catalytic reaction. Also, the pellets of the catalyst preferably have a length of 1 to 10 mm and a diameter of 2 to 6 mm, and are useful for catalyst-fixed bed type catalytic reaction.

In the embodiment (3), the hydrogenation reaction of the epoxidized $C_6$–$C_{12}$ cyclohydrocarbon compounds may be carried out in the liquid reaction medium as mentioned above.

In the method of the present invention, the reaction time is variable in response to the reaction temperature, the hydrogen pressure, the type and amount of the catalyst and the concentrations of the starting material and hydrogen in the reaction system. Usually, the hydrogenation reaction is completed within about 0.1 to about 5 hours, particularly 1 to 3 hours.

EXAMPLES

The present invention will be further illustrated by the following examples in comparison with the comparative Examples.

Example 1

A stainless steel autoclave having a capacity of 100 ml and equipped with an agitator was charged with 1.82 g (10 millimoles) of epoxycyclododecane, 16.4 g of cyclohexane and 0.46 g of a 5 wt % Pd/C catalyst (corresponding to 0.216 millimole in terms of palladium atoms).

The 5 wt % Pd/C catalyst refers to a catalyst comprising palladium, as a catalytic metal component, in an amount of 5% by weight and a carrier consisting of activated carbon in an amount of 95% by weight based on the total weight of the catalyst. The reaction mixture in the autoclave was pressurized with hydrogen gas at room temperature to a pressure of 0.98 MPa on gauge, and then heated to a temperature of 100° C., and maintained at this temperature under the pressure of 0.98 MPa on gauge for one hour, while agitating the reaction mixture. After the reaction procedure was completed, the reaction mixture was cooled to room temperature, the catalyst was removed from the reaction mixture by filtering. The resultant reaction product-containing liquid was subjected to an analysis. The analysis was carried out by a gas chromatography. As a result, it was confirmed that the reaction product contains cyclododecanol (which will be referred to as CDOL hereinafter) in a yield of 72 molar % and cyclododecanone (which will be referred to as CDON hereinafter) in a yield of 14 molar %. The total yield of CDOL and CDON was 86 molar %.

Examples 2 to 6 and Comparative Examples 1 to 2

In each of Examples 2 to 6 and Comparative Examples 1 to 2, CDOL and CDON were produced by the same procedures as in Example 1, except that the type of the catalyst, the hydrogen pressure for reaction, the reaction temperature and the reaction time were changed as shown in Table 1. The results are shown in Table 1.

TABLE 1

|  |  | Catalyst | Reaction temperature (° C.) | Reaction hydrogen pressure (MPa·G) | Reaction time (h) | Yield of CDOL (%) | Yield of CDON (%) | Total yield of CDOL and CDON (%) |
|---|---|---|---|---|---|---|---|---|
| Example | 2 | 5 wt % Pd/C | 125 | 0.98 | 1 | 52 | 15 | 67 |
|  | 3 | 5 wt % Pd/C | 150 | 0.98 | 1 | 40 | 19 | 59 |
|  | 4 | 5 wt % Pd/C | 125 | 5.4 | 3 | 84 | 7 | 91 |
| Comparative Example | 1 | 5 wt % Pd/C | 50 | 0.98 | 1 | 3 | 3 | 6 |
|  | 2 | 5 wt % Pd/C | 100 | 0.098 | 1 | 5 | 1 | 6 |
| Example | 5 | 5 wt % Ru/C | 100 | 1.96 | 2 | 47 | 2 | 49 |
| Example | 6 | 5 wt % Pd/C | 125 | 5.4 | 2 | 83 | 10 | 93 |

Example 7

A stainless steel autoclave having a capacity of 100 ml and equipped with an agitator was charged with 10.01 g (56.2 millimoles of 1,2-epoxy-5,9-cyclododecadiene, log of cyclohexane and 0.50 g of a wt % Pd/C catalyst (corresponding to 0.235 millimole in terms of palladium atoms).

The reaction mixture in the autoclave was pressurized with a hydrogen gas at room temperature to a pressure of 4.9 MPa on gauge, and then heated to a temperature of 125° C., and maintained at this temperature under the pressure of 4.9 MPa on gauge for one hour, while agitating the reaction mixture. After the reaction procedure was completed, the reaction mixture was cooled to room temperature, the catalyst was removed from the reaction mixture by filtering. The resultant reaction product-containing liquid was subjected to an analysis. The analysis was carried out by a gas chromatography. As a result, it was confirmed that the reaction product contains CDOL in a yield of 92 molar % and CDON in a yield of 5 molar %. The total yield of CDOL and CDON was 97 molar %.

In Examples 1 to 7, it was confirmed that, in accordance with the method of the present invention, cyclododecanol and cyclododecanone could be produced in a high total yield by bringing hydrogen into contact with at least one monoepoxy $C_{12}$ cyclohydrocarbon compound, for example, epoxycyclododecane, epoxycyclododecacene and/or epoxycyclododecadiene, in the presence of a platinum group metal-containing catalyst under a specific pressure of 0.1 to 5.5 MPa at a temperature of 100 to 280° C.

Example 8

A glass autoclave having a capacity of 300 ml and equipped with an agitator was charged with 100 g (0.562 mole) of 1,2-epoxy-5,9-cyclododecadiene and 1.0 g of a 5 wt % Pd/silica catalyst in which palladium was carried, in an amount of 5% by weight on a silica carrier and 0.47 millimole of palladium was contained.

The reaction mixture in the autoclave was pressurized with hydrogen gas to a pressure of 0.294 MPa on gauge at room temperature, heated to a temperature of 175° C. and held at this temperature for 5 hours while maintaining the hydrogen pressure at the level of 0.294 MPa and agitating the reaction mixture.

After the reaction procedure was completed, the reaction mixture was cooled to room temperature and filtered to remove the catalyst from the reaction product liquid. The reaction product liquid was subjected to an analysis.

The analysis of the reaction product liquid was effected by a gas chromatography. As a result, it was found that the 1,2-epoxy-5,9-cyclododecadiene was consumed in an amount of 100%, cyclododecanone (CDON) was obtained in a yield of 85.5 molar %, epoxycyclododecane (which will be referred to as ECD hereinafter) in 10.6 molar % and cyclododecanol (CDOL) in 0.9 molar %.

The reaction product liquid further contained cyclododecane (which will be referred to as CDAN hereinafter) and other high boiling temperature substances as by-products.

The reaction results are shown in Table 2.

Examples 9 to 15

In each of Examples 9 to 15, a hydrogenation of 1,2-epoxy-5,9-cyclododecadiene was carried out by the same procedure as in Example 8, except that the type of the catalyst, the reaction hydrogen pressure, the reaction temperature and the reaction time were changed as shown in Table 2. The analysis results of the resultant: reaction product liquid are shown in Table 2.

In all of the examples, the 1,2-epoxy-5,9-cyclododecadiene used as a starting material was consumed in an amount of 100%.

TABLE 2

| | | Catalyst | Reaction temperature & time | Hydrogen pressure (MPa·G) | Yields of products (molar %) | | | Yields of by-products (molar %) | |
|---|---|---|---|---|---|---|---|---|---|
| | | | | | CDON | ECD | CDOL | CDAN | Others |
| Example | 8 | 5 wt % Pd/silica | 175° C. 5 h | 0.294 | 85.5 | 10.6 | 0.9 | 0.2 | 2.3 |
| | 9 | 5 wt % Pd/silica | 175° C. 3 h | 0.588 | 82.3 | 14.4 | 1.2 | 0.2 | 1.5 |
| | 10 | 5 wt % Pd/silica | 160° C. 2 h | 0.882 | 81.6 | 15.5 | 1.2 | 0.3 | 0.7 |
| | 11 | 5 wt % Pd/alumina | 160° C. 2 h | 0.882 | 72.9 | 24.2 | 1.9 | 0.3 | 0.8 |
| | 12 | 5 wt % Pd/C | 160° C. 2 h | 0.98 | 68.4 | 27.0 | 3.6 | 0.3 | 0.3 |
| | 13 | 5 wt % Pd/zeolite | 160° C. 2 h | 0.882 | 69.4 | 27.5 | 1.8 | 0.5 | 1.0 |
| | 14 | 5 wt % Pd/silica-alumina | 160° C. 2 h | 0.882 | 70.7 | 25.5 | 2.4 | 0.3 | 1.4 |
| | 15 | 5 wt % Pd/alumina | 100° C. 7 h | 0.98 | 63.3 | 33.2 | 2.3 | 0.2 | 0.9 |

Example 16

A SUS autoclave having a capacity of 100 ml and equipped with an agitator was charged with 20 g (0.112 mole) of 1,2-epoxy-5,9-cyclododecadiene and 0.2 g of a 5 wt % Pd/alumina catalyst in which palladium was carried, in an amount of 5% by weight on an alumina carrier and 0.06 millimole of palladium was contained.

The reaction mixture in the autoclave was pressurized with hydrogen gas to a pressure of 0.98 MPa on gauge at room temperature, heated to a temperature of 200° C. and held at this temperature for one hour while maintaining the hydrogen pressure at the level of 0.98 MPa and agitating the reaction mixture.

After the reaction procedure was completed, the reaction mixture was cooled to room temperature and filtered to remove the catalyst from the reaction product liquid. The reaction product liquid was subjected to analysis.

The analysis of the reaction product liquid was effected by a gas chromatography. As a result, it was found that the 1,2-epoxy-5,9-cyclododecadiene was consumed in an amount of 100%, cyclododecanone (CDON) was obtained in a yield of 74.7 molar %, epoxycyclododecane (which will be referred to as ECD hereinafter) in 20.5 molar % and cyclododecanol (CDOL) in 2.7 molar %.

The reaction product liquid further contained cyclododecane (which will be referred to as CDAN hereinafter) and other high boiling temperature substances as by-products.

The reaction results are shown in Table 2.

Examples 17 and 18 and Comparative Example 3

In each of Examples 17 and 18 and comparative Example 3, the same hydrogenation procedure as in Example 16 was carried out, except that the type of the catalyst, the reaction hydrogen pressure, the reaction temperature and the reaction time were as shown in Table 3. The resultant reaction product liquid was analyzed in the same manner as in Example 8.

The analysis results are shown in Table 3. In each of the examples and comparative examples, the 1,2-epoxy-5,9-cyclododecadiene was consumed in an amount of 100%.

TABLE 3

| | | Catalyst | Reaction temperature & time | Hydrogen pressure (MPa·G) | Yields of products (molar %) | | | Yields of by-products (molar %) | |
|---|---|---|---|---|---|---|---|---|---|
| | | | | | CDON | ECD | CDOL | CDAN | Others |
| Example | 16 | 5 wt % Pd/alumina | 200° C. 1 h | 0.98 | 74.7 | 20.5 | 2.7 | 0.4 | 1.6 |
| | 17 | 5 wt % Pd/alumina | 245° C. 1 h | 0.98 | 79.4 | 7.1 | 8.7 | 1 | 3.9 |
| | 18 | 5 wt % Pd/alumina | 160° C. 1 h | 1.96 | 60.4 | 35.1 | 3.1 | 0.2 | 1.3 |
| Comparative Example | 3 | 5 wt % Pd/alumina | 50° C. 3 h | 0.98 | 3.7 | 90.6 | 5 | 0 | 0.7 |

Comparative Example 4

The same hydrogenation procedure and analysis as in Comparative Example 3 were carried out, except that after the same reaction procedure as in Comparative Example 3 was completed, the reaction mixture was further heated at a temperature of 160° C. under the pressure of 0.98 MPa on gauge for 2 hours.

In the analysis results, CDON was obtained in a yield of 3.9 molar %, ECD in 90.5 molar %, and CDOL in 5.5 molar %.

In Examples 8 to 18, it was confirmed that in accordance with the method of the present invention, 1,2-epoxy-5,9-cyclododecadiene could be hydrogenated with hydrogen by a single-step reaction in the presence of a platinum group metal-containing catalyst, to produce cyclododecanone with a high yield.

Example 19

Activated alumina particles having an average particle size of 15 μm were calcined in the ambient air atmosphere at a temperature of 1300° C. for 3 hours, to prepare alumina particles having a specific surface area of 8 m²/g. By an X-ray diffractometry, it was confirmed that the calcined alumina particles are α-alumina (α-$Al_2O_3$) particles having fine pores with an average pore size of 160 nm. The α-alumina particles are suspended in water, an aqueous solution of palladium chloride ($PdCl_2$) was added in an amount of palladium of 5% by weight, based on the weight of the α-alumina, to the aqueous α-alumina suspension. The mixture was heated, while agitating the evaporate away water from the mixture. The dried mixture was reduced with hydrogen at a temperature of 300° C., to provide a catalyst in which Pd is carried in an amount of 5% by weight on the α-alumina particle carrier.

An autoclave having a capacity of 100 ml was charged with 10.0 g of epoxycyclododecadiene, 10.0 g of cyclohexane and 0.20 g of the above-mentioned powdery catalyst; hydrogen gas was introduced into the autoclave under a pressure of 0.882 MPa; and then the reaction mixture in the autoclave was subjected to a hydrogenation reaction at a temperature of 160° C. for one hour, while agitating the reaction mixture under the above-mentioned pressure.

After the reaction was completed, the catalyst was removed from the reaction product mixture by filtering, and the reaction product mixture was subjected to gas chromatographic analysis. As a result, it was found that cyclododecanol was obtained in a yield of 6 molar % based on the fed epoxycyclododecadiene, and cyclododecanone was obtained in a yield of 76 molar %. Thus, the total yield of cyclododecanol and cyclododecanone was 82 molar %. In the reaction, epoxycyclododecane was produced in a yield of 16 molar %.

Example 20

An autoclave having a capacity of 100 ml was charged with 10.0 g of epoxycyclododecadiene, 10.0 g of cyclohexane and 0.20 g of the same catalyst as in Example 19; the reaction mixture was pressurized with a hydrogen gas at a pressure of 4.9 MPa, and subjected to a hydrogenation reaction at a temperature of 200° C. under the above-mentioned pressure for 2 hours, while agitating the reaction mixture.

After the reaction was completed, the catalyst was removed from the reaction product mixture by filtering, and the resultant reaction product mixture was subjected to the gas chromatographic analysis. As a result, it was found that cyclododecanol was obtained in a yield of 53 molar % and cyclododecanone was obtained in a yield of 20 molar %, based on the molar amount of the fed epoxycyclododecadiene. The total yield of cyclododecanol and cyclododecanone was 73 molar %.

Example 21

A catalyst was prepared by the same procedures as in Example 19, except that the amount of palladium carried on the α-alumina carrier was changed from 5% to 3% by weight.

The same hydrogenation procedure as in Example 19 was carried out except that the above-mentioned 3 wt % Pd/α-alumina catalyst was employed. In the gas chromatographic analysis results, cyclododecanol was obtained in a yield of 4 molar %, and cyclododecanone in a yield of 71 molar %. The total yield of cyclododecanol and cyclododecanone was 75 molar %.

Example 22

The same hydrogenation procedure and analysis as in Example 19 were carried out, except that after the same reaction as in Example 19 was completed, the resultant reaction mixture was subjected to a further reaction procedure at a temperature of 200° C. under a hydrogen pressure of 4.9 MPa for 2 hours. The catalyst was removed from the reaction product mixture by filtering, and the reaction product mixture was subjected to the gas chromatographic analysis. As a result, it was found that cyclododecanol was obtained in a yield of 18 molar % and cyclododecanone in a yield of 75 molar %. The total yield of cyclododecanol and cyclododecanone was 93 molar %.

Example 23

The same hydrogenation procedures and analysis as in Example 19 were carried out, except that in the preparation of the 5 wt % Pd/aluminum catalyst, the activated alumina was not calcined and was directly used as a carrier for the palladium, and the hydrogenation procedure was carried out in the presence of the 5 wt % Pd/non-calcined activated alumina. As a result, the resultant reaction product mixture contained cyclododecanol in a yield of 7 molar % and cyclododecanone in a yield of 56 molar %. The total yield of cyclododecanol and cyclododecanone was 63%.

Example 24

The same hydrogenation procedure and analysis as in Example 19 were carried out, except that in the preparation of the catalyst, magnesia (MgO) particles were employed as a carrier particles in place of the α-alumina particles, and the hydrogenation reaction was effected in the presence of a catalyst in which 5 wt % of palladium were carried on the magnesia particle carrier. As a result, the reaction product mixture contained cyclododecanol in a yield of 5 molar % and cyclododecanone in a yield of 47 molar %. Thus, the total yield of cyclododecanol and cyclododecanone was 52% by weight.

Example 25

The same hydrogenation procedure and analysis as in Example 19 were carried out, except that in the preparation of the catalyst, titania ($TiO_2$) particles were employed as a carrier particles in place of the α-alumina particles, and the hydrogenation reaction was effected in the presence of a catalyst in which 5 wt % of palladium were carried on the titania particle carrier. As a result, the reaction product mixture contained cyclododecanol in a yield of 5 molar % and cyclododecanone in a yield of 58 molar %. Thus, the total yield of cyclododecanol and cyclododecanone was 63% by weight.

Example 26

The same hydrogenation procedure and analysis as in Example 19 were carried out, except that in the preparation of the catalyst, silica ($SiO_2$) particles were employed as a carrier particles in place of the α-alumina particles, and the hydrogenation reaction was effected in the presence of a catalyst in which 5 wt % of palladium were carried on the silica particle carrier. As a result, the reaction product mixture contained cyclododecanol in a yield of 20 molar % and cyclododecanone in a yield of 45 molar %. Thus, the total yield of cyclododecanol and cyclododecanone was 65% by weight.

The analysis results are shown in Table 4.

TABLE 4

| | | | Reaction conditions | | | Reaction products | | |
|---|---|---|---|---|---|---|---|---|
| | | | | | | Yield | Yield | Total yield |
| Example No. | Item | Type of catalyst | Reaction temperature (° C.) | Hydrogen pressure (MPa) | Reaction time (hr) | of CDOL (%) | of CDON (%) | of CDOL and CDON (%) |
| Example | 19 | 5 wt % Pd /α-$Al_2O_3$ | 160 | 0.882 | 1 | 6 | 76 | 82 |
| | 20 | 5 wt % Pd /α-$Al_2O_3$ | 200 | 4.9 | 2 | 53 | 20 | 73 |
| | 21 | 3 wt % Pd /α-$Al_2O_3$ | 160 | 0.882 | 1 | 4 | 71 | 75 |
| | 22 | 5 wt % Pd /α-$Al_2O_3$ | 160 200 | 0.882 4.9 | 1 2 | 18 | 75 | 93 |
| | 23 | 5 wt % Pd /activated α-$Al_2O_3$ | 160 | 0.882 | 1 | 7 | 56 | 63 |
| | 24 | 5 wt % Pd /MgO | 160 | 0.882 | 1 | 5 | 47 | 52 |
| | 25 | 5 wt % Pd /$TiO_2$ | 160 | 0.882 | 1 | 5 | 58 | 63 |
| | 26 | 5 wt % Pd /$SiO_2$ | 160 | 0.882 | 1 | 20 | 45 | 65 |

Note:
CDOL . . . Cyclododecanol
CDON . . . Cyclododecanone

Table 4 shows that in the platinum group metal-containing catalyst, the carrier comprising α-alumina contributes to increasing the total yield of cyclododecanol and cyclododecanone.

What is claimed is:

1. A single step hydrogenation method for epoxidized unsaturated $C_6$–$C_{12}$ cyclohydrocarbon compounds, comprising a single step of bringing an epoxidized unsaturated cyclohydrocarbon compound having 6 to 12 carbon atoms into contact with hydrogen under a hydrogen pressure of 0.1 to 5.4 Mpa gauge at a temperature of 100 to 280° C. in the presence of a catalyst comprising a catalytic metal component comprising at least one platinum group metal carried on a solid inert carrier to convert the epoxidized unsaturated $C_6$–$C_{12}$ cyclohydrocarbon coumpound to $C_6$–$C_{12}$ cycloalkanone and $C_6$–$C_{12}$ cycloalkanol.

2. The single step hydrogenation method of claim 1, wherein the epoxidized unsatureated $C_6$–$C_{12}$ cyclohydrocarbon compound comprises at least one member selected from the group consisting of monoepoxy $C_6$–$C_{12}$ cycloalkenes and monoepoxy $C_6$–$C_{12}$ cycloalkadienes.

3. The single step hydrogenation method of claim 1, wherein the catalytic metal component of the catalyst comprises at least one member selected from the group consisting of ruthenium, palladium, and platinum.

4. The single step hydrogenation method of claim 1, wherein the solid inert carrier comprises at least one member selected from the group consisting of activated carbon, alumina, silica, silica-alumina, titania, zeolites and spinel.

5. The single step hydrogenation method of claim 1, wherein the catalytic metal component of the catalyst is in an amount of 0.1 to 20% by weight based on the weight of the inert carrier.

6. The single step hydrogenation method of claim 1, wherein the catalyst is present in an amount, in terms of the platinum group metal, of 0.00001 to 0.1 mole per mole of the starting material.

7. The single step hydrogenation method of claim 1, wherein the epoxidized unsaturated $C_6$–$C_{12}$ cyclohydrocarbon compound comprises at least one member selected from the group consisting of monoepoxy cyclododecenes and monoepoxy cyclododecadienes, and the epoxidized unsaturated $C_6$–$C_{12}$ cyclohydrocarbon compound is brought into contact with hydrogen under a hydrogen pressure of 0.1 to 5.4 MPa gauge at a temperature of 100 to 280° C. in the presence of a catalyst comprising a catalytic metal component comprising at least one metal selected from the group consisting of palladium and ruthenium, and carried on a solid inert carrier, to produce cyclododecanol and cyclododecanone.

8. The single step hydrogenation method of claim 1, wherein the expoxidized unsaturated $C_6$–$C_{12}$ cyclohydrocarbon compound comprises 1,2-epoxy-5,9-cyclododecadiene and is brought into contact with hydrogen under a hydrogen pressure of 0.1 to 3.9 MPa gauge at a temperature of 100 to 280° C., in the presence of a catalyst comprising, as a catalytic metal component, at least one platinum group metal, carried on a solid inert carrier to produce cyclododecanone.

9. The single step hydrogenation method of claim 1, wherein the the solid inert carrier comprises α-alumina, and the epoxidized unsaturated $C_6$–$C_{12}$ cyclohydrocarbon compound is hydrogenated into a mixture of $C_6$–$C_{12}$ cycloalkanone and $C_6$–$C_{12}$-cycloalkanol.

* * * * *